United States Patent [19]

Onishi et al.

[11] Patent Number: 4,623,250

[45] Date of Patent: Nov. 18, 1986

[54] DC PLASMA JET GENERATOR FOR EMISSION SPECTROCHEMICAL ANALYSIS

[75] Inventors: Koichi Onishi; Takashi Suganuma, both of Katsuta, Japan

[73] Assignee: Doryokuro Kakunenryo Kaihatsu Jigyodan, Tokyo, Japan

[21] Appl. No.: 530,122

[22] Filed: Sep. 7, 1983

[30] Foreign Application Priority Data

Oct. 12, 1982 [JP] Japan ................... 57-178779

[51] Int. Cl.⁴ ............................. G01N 21/73
[52] U.S. Cl. ................... 356/316; 313/231.61; 313/152; 219/121 PR; 219/121 P; 219/138; 373/91; 373/93
[58] Field of Search .............. 219/75, 121 P, 121 PM, 219/121 PR, 121 PS, 121 PW, 136, 138, 139; 313/231.41, 231.61, 152; 356/311, 313, 316; 373/91, 92, 93

[56] References Cited

U.S. PATENT DOCUMENTS

| | | | |
|---|---|---|---|
| 2,344,719 | 3/1944 | Nusbaum et al. | 313/152 |
| 3,484,650 | 12/1969 | Rendina | 356/316 |
| 4,009,413 | 2/1977 | Elliott et al. | 356/316 |
| 4,024,337 | 5/1977 | Andersson et al. | 373/93 |
| 4,147,957 | 4/1979 | Hildebrand | 356/316 |

OTHER PUBLICATIONS

"A Unique Approach to Atomic Spectroscopy High Energy Plasma Excitation and High Resolution Spectrometry," Reednick, Joseph, *American Laboratory*, vol. 11, No. 3, Mar. 1979, pp. 53-62.
"A Remote-Controlled Stand," Raag, F. I., *Industrial Laboratory*, vol. 42, No. 4, pp. 583-584, Apr. 1976.

*Primary Examiner*—F. L. Evans
*Assistant Examiner*—Joel L. Harringa
*Attorney, Agent, or Firm*—Wenderoth, Lind & Ponack

[57] ABSTRACT

Improvements on a DC plasma jet generator for emission spectrochemical analysis wherein two anode blocks and one cathode block are positioned in an inverted Y shape, and each of the anode blocks has a cylinder, a piston, an anode received by a recess in the end of the piston. Each anode can be secured in the recess at the end of the piston in the corresponding anode block by magnetic force. Each of the anode and cathode blocks is pivotable so that the associated electrode attached to each block can be fixed upright with the free end thereof directed upward. This means that the electrodes can be replaced easily as well as speedily by remote control using manipulators.

4 Claims, 6 Drawing Figures

DC PLASMA JET GENERATOR FOR EMISSION SPECTROCHEMICAL ANALYSIS

BACKGROUND OF THE INVENTION

The present invention relates to a plasma jet generator for use in DC (direct current) plasma spectrochemical analysis, and more particularly to a plasma jet generator wherein electrodes can be replaced by using a manipulator, which is useful for, e.g., analysis within a hot cell or a glove box in research in the nuclear power field, although it is not especially limited thereto.

Analyses in research on high-level radioactive materials in fields related to nuclear power must be remote-controlled analyses employing a hot cell shut off from their surroundings. However, since conventional analyses such as titration, colorimetric and similar analyses are analytical operations originally intended to be carried out in laboratories, it is difficult to apply these analyses to in-cell analytical methods. In addition, these analyses have a disadvantageously complicated analytical operation and use a wide variety of reagents although the range of subjects to be analyzed is narrow. Moreover, a long period of time is required for these analyses.

Emission spectrochemical analysis wherein an analytical sample is excited so as to emit light, and the emission spectrum wavelengths and the spectral line intensities are measured to identify the components of the analytical sample and their concentrations is simple in operation, has a high detection sensitivity, and can measure a wide range of concentrations, so that it provides the advantage that several elements can be analyzed simultaneously. Moreover, since the principle of emission spectrochemical analysis is based on the measurement of light, it is possible to effect stable measurements independent of high-level radioactive rays which are a large obstructive factor in hot cells. Therefore emission spectrochemical analysis is the most suitable as an in-cell analytical method.

A typical DC plasma emission spectrometer, as shown in FIG. 1, comprises a DC plasma jet generator (light-emitting unit) 1, a spectroscope 2, a detection unit 3 and a data processing unit, as well as other elements. This DC plasma emission spectrometer is a conventionally-known simultaneous multi-element instrument wherein an analytical sample is introduced into a high-temperature DC plasma so that it is excited to emit light, and its emission spectral lines are detected by a spectroscope in order to identify and quantify the elements in the sample from the spectral lines and their intensities. Incidently, reference numeral 4 in FIG. 1 designates an outlet slit placed in the focal plane of the spectrum.

In this case, the DC plasma jet generator 1 has a construction, as clearly shown in FIG. 2, such that two anode blocks 10 and one cathode block 11 are positioned in an inverted Y shape. A graphite electrode 12 (e.g., of dimensions 2.3 mm diameter and 46.6 mm length) is employed as each of the anodes, while a tungsten electrode 13 (e.g., of dimensions 1 mm diameter and 61 mm length) is employed as the cathode. Reference numeral 14 denotes ceramic sleeves mounted over each electrode block. To ignite the plasma, argon is blown in from the electrode blocks 10 and 11, and the graphite electrodes 12 and the tungsten electrode 13 are pushed out from their respective ceramic sleeves 14 so as to come in contact with each other and make a discharge. When the plasma has ignited, the three electrodes are withdrawn into their respective ceramic sleeves 14, and the ionization of the argon is maintained to form a plasma 15. An analytical sample nebulized by a nebulizer (not shown) is introduced into the plasma 15 through a sample-introducing tube 16 made of quartz, and is thus excited to emit light.

A typical conventional anode block is shown in FIG. 3 in detail. The anode block comprises a cylinder 20, a water-cooled cooling block 21 mounted on the end of the cylinder 20, a piston 22 reciprocatable in the cylinder 20, a spring 23 housed in the cylinder 20 together with the piston 22, and the ceramic sleeve 14 attached to the end of the cooling block 21. The piston 22 is advanced by the pressure of the argon blown in from the base end or the proximal end of the cylinder 20, and is retracted by the force of the coiled spring 23 when the supply of argon is stopped. A recess 24 formed in the distal end of the piston holds the graphite electrode 12. The graphite electrode 12 is inserted into the piston end recess 24 and is rotated through about 90 degrees, so that a cut portion 25 at the proximal end of the graphite electrode 12 is secured therein. The removal of the graphite electrode 12 is effected by a similar manual operation, i.e., by rotating it through 90 degrees. These operations depend a great deal on the sensitivity of the operator. The ceramic sleeve 14 is removed whenever the electrode is replaced.

This conventional DC plasma emission spectrometer is an analytical instrument which is effective when used in an ordinary laboratory, as mentioned before. It is, however, impossible to carry out any analysis by installing such an instrument in a hot cell without modification. This is because the interior of a hot cell is a bad environment which has both a high temperature and a high humidity and includes acid vapors, etc., which presents problems in the maintenance and management of the instrument. Another reason is that it is difficult to effect the operation and maintenance of the elements and members of the instrument using manipulators. Accordingly methods have been examined in which the spectroscope, data processing unit, etc., including the complicated optical systems and electrical circuits, are installed outside the cell, the DC plasma jet generator is installed inside the cell, and the optical data on the inside of the cell is extracted out of the cell. In such a case, the electrodes must be replaced periodically since they wear out during the operation of the plasma jet generator. Since it is impossible to check the degree of wear of each electrode when a DC plasma jet generator is operating in a hot cell, the electrodes must be replaced virtually every day (every time the instrument is used). However, the electrode parts are very slender, and in particular the replacement of the graphite electrodes involves an extremely high probability of breaking them since the fragile graphite is removed and attached mechanically. Therefore the replacement operation requires some training, as it does even in an ordinarily laboratory. Moreover, it is usually impossible to remove a broken electrode without disassembling the associated anode block. Although, in order to operate a plasma jet generator in a hot cell, it is necessary to make it possible to replace the electrodes required for the generation of the plasma by remote control using manipulators, such remote control is impossible in the prior art described above.

SUMMARY OF THE INVENTION

It is, therefore, an object of the invention to provide a DC plasma jet generator which can be placed in a hot cell and be operated as well as maintained by remote control from the outside of the hot cell using manipulators.

It is another object of the invention to provide a DC plasma jet generator which is improved so that the graphite anode electrodes thereof can be easily as well as speedily removed and attached by manipulators.

It is still another object of the invention to provide a DC plasma jet generator provided with graphite anode electrodes having such a structure that the production cost can be reduced.

Briefly, the invention provides improvements in a conventional DC plasma jet generator wherein two anode blocks and one cathode block are positioned in an inverted Y shape, each of the anode blocks has a cylinder, a cooling block mounted on the end of the cylinder, a piston reciprocatable in the cylinder, and an anode electrode attached into a recess formed at the distal end of the piston.

One of the improvements is in the structures of the piston and the anode electrode of each anode block. More specifically, the piston of each anode block has a magnet made of a rare earth metal embedded in the bottom of the end recess thereof. The anode electrode is formed by attaching a graphite rod to the distal end of a magnetic metal rod. Thus, when the base end or the proximal end of the magnetic metal rod portion of the anode electrode is inserted into the recess at the end of the piston, the two of them are secured to each other by magnetic force.

Another improvement provided by the invention is that the two anode blocks and one cathode block are installed rotatably. More specifically, each electrode block is able to pivot so that each electrode attached to the corresponding block can be fixed upright with the free end or the distal end of the electrode directed upward. With the electrodes held upright in this way, their replacement can be conducted easily as well as speedily by remote control using manipulators.

The above and other objects, features, and advantages of the invention will become apparent from the following description of an embodiment with reference to the accompanying drawings.

DETAILED DESCRIPTION OF THE INVENTION

Figure 1:
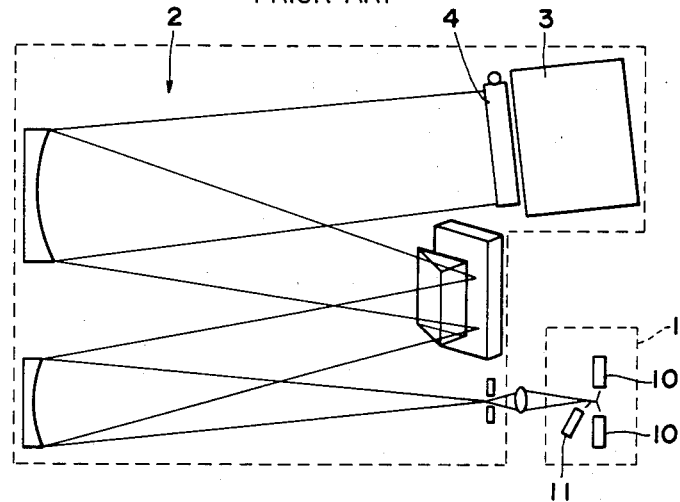
FIG. 1 is a schematic diagram of a common DC plasma emission spectrometer.
Figure 2:
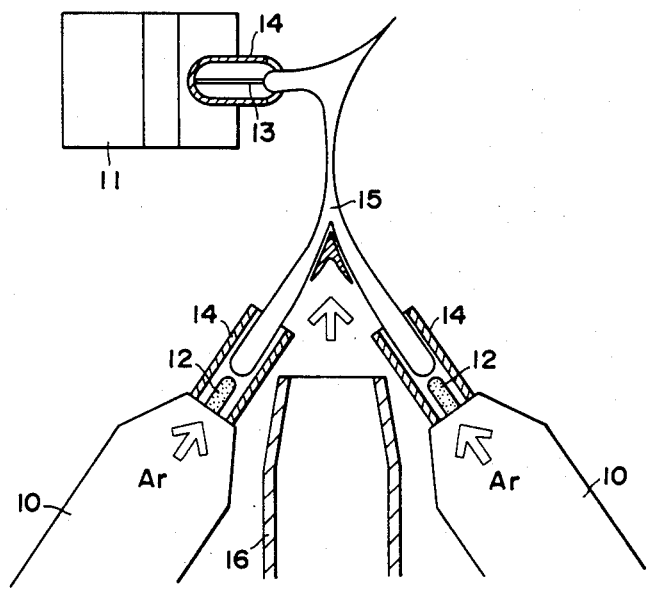
FIG. 2 illustrates the operation of the DC plasma jet generator employed in the spectrometer of FIG. 1.
Figure 3:
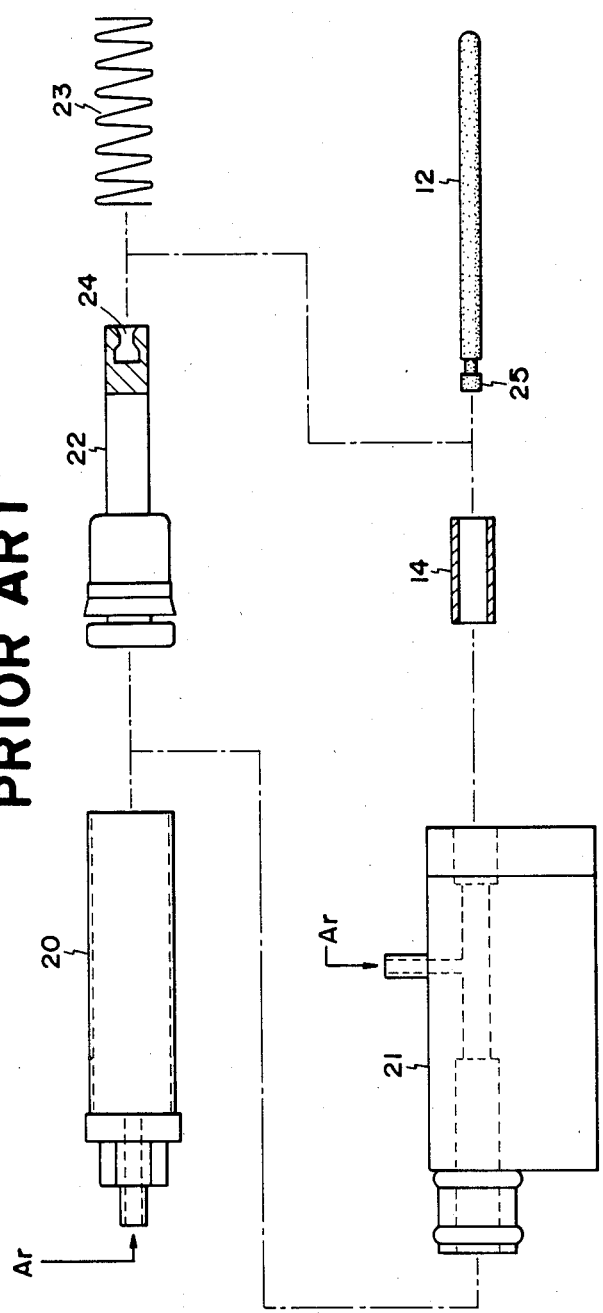
FIG. 3 is an exploded view of a conventional anode block employed in the DC plasma jet generator.
Figure 4:
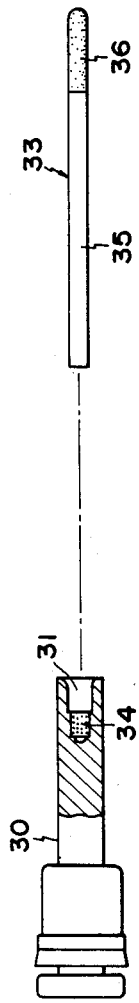
FIG. 4 illustrates an anode block and a piston employed in a DC plasma jet generator in accordance with the invention.

FIG. 4 illustrates an embodiment of the anode block parts employed in the invention. Since the basic construction of the anode block 10 can be substantially the same as that of the conventional block shown in FIG. 3, except for the piston and the graphite electrode, illustration of the parts other than the piston and the graphite electrode is omitted. In the invention, the graphite electrode is secured, not mechanically as hitherto, but magnetically by the use of a magnet. In FIG. 4, a piston 30 is machined to the same dimensions as those of a conventional piston (represented by reference numeral 22 in FIG. 3) except for the end recess portion. An end recess 31 at the distal end of the piston 30 has a configuration which fits the base end or the proximal end of an electrode 33 exactly, and is provided with a magnet 34 made of a rare earth metal embedded in the bottom portion of the end recess 31. The electrode 33 is formed by driving a graphite rod portion 36 having a length of about 10 mm into the distal end of a rod of magnetic metal 35, e.g., an iron rod. The overall dimensions of the electrode 33 are the same as those of the conventional one shown in FIG. 3. Accordingly, the magnetic metal rod 35 portion of the electrode 33 can be gripped easily by a manipulator, and there is no possibility of the electrode breaking when it is gripped this way. By simply inserting the magnetic metal rod portion at the base end or the proximal end of the electrode 33 into the piston end recess 31, the electrode 33 is secured by magnetic force, and the loading of the graphite electrode is complete. Removal of the electrode is also carried out easily by the manipulator, since it is only necessary to draw the electrode 33 out of the piston end recess 31.

The length (about 10 mm) of the graphite rod portion 36 is a dimension determined by experiments. It has been confirmed that a length of the order of 10 mm is sufficient for an analysis, and such a length makes it possible, if the graphite rod portion 36 breaks, to grip the distal end of the magnetic metal rod 35 from the outside of the anode block. Therefore, if the graphite rod portion 36 breaks, it is totally unnecessary to disassemble the electrode block, and the mounting and removal of the elctrodes can be accomplished speedily, easily and reliably.

The reason for employing a rare earth metal as the material of the magnet 34 in the invention is as follows. The usual ferrite magnets cannot be used in heat-generating portions such as a light-emitting part owing to the thermal demagnetization characteristics thereof, and cannot be used in an electrode part requiring electrical conductivity owing to their large specific electrical resistance. On the other hand, a magnet made of a rare earth metal has an excellent heat resistance and specific electrical resistance, and has an energy product two to five times as large as that of a ferrite magnet, and hence is suitable for use as a magnet in a very small component.

Figure 5:
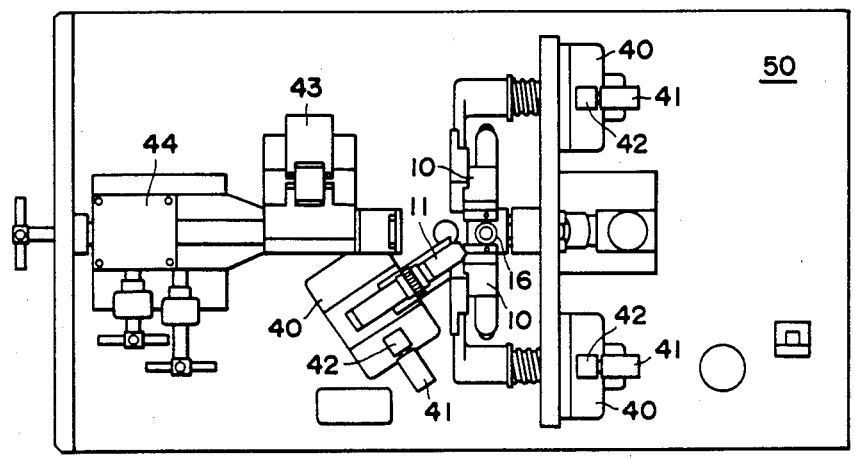
FIG. 5 is a plan view of DC plasma jet generator for a hot cell in accordance with the invention, showing an arrangement of a plasma-igniting position.
Figure 6:
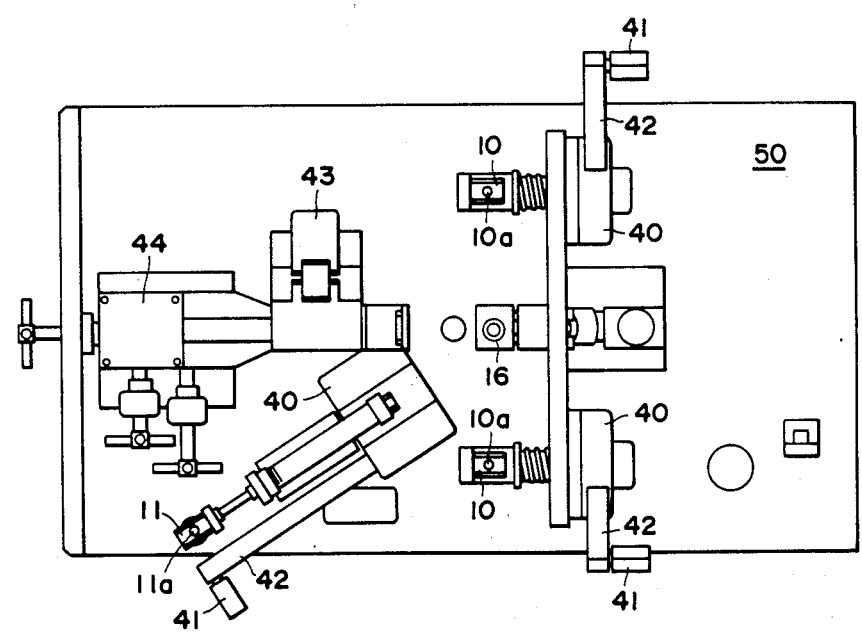
FIG. 6 is a plan view of the DC plasma jet generator of FIG. 5, showing an arrangement of an electrode-replacing position.

The invention contrives not only an improvement in the piston and the electrode, but also a means for further speeding up and facilitating the operations of mounting and removing electrodes. FIGS. 5 and 6 in combination illustrate the DC plasma jet generator installed in a hot cell (not shown). FIG. 5 shows the DC plasma jet generator in operation (when the plasma is ignited); therefore, the electrodes of the anode blocks 10 and the cathode block 11 are withdrawn into the corresponding ceramic sleeves. FIG. 6 shows the DC plasma jet generator when the electrodes are being replaced.

Each of the two anode blocks 10 and one cathode block 11 is supported by a respective rotary ratchet mechanism 40 mounted on a frame 50, and can be pivoted between two positions, a plasma-igniting position (shown in FIG. 5) and an electrode-replacing position (shown in FIG. 6), and can be positioned and fixed in either of the positions by using a manipulator to move an arm 42 by the operation of a handle 41. In the electrode-replacing position shown in FIG. 6, the electrode blocks 10 and 11 have been pivoted until the electrodes attached to each of the electrode blocks 10 and 11 are upright with their free ends or distal ends directed upward. In other words, in this position electrode-receiving holes 10a and 11a in the corresponding electrode blocks 10 and 11 open upward, and in addition the distance between the electrode blocks is much larger, so that the electrode-replacing operation becomes extremely easy. The electrode-receiving hole 10a of each of the anode blocks 10 corresponds to the opening of the piston end recess 31 shown in FIG. 4.

In FIGS. 5 and 6, reference numeral 16 denotes a sample-introducing tube, numeral 43 designates a mechanism for attaching and removing an optical fiber for transmitting the obtained emission spectrum of the analytical sample to a spectroscope outside the cell, and numeral 44 represents an optical fiber fine adjustment device.

Since the DC plasma jet generator of the invention has the construction described above, it is possible to attach and remove the graphite electrodes by manipulators, which is conventionally considered to be impossible. If a graphite electrode breaks, the electrode can be removed without requiring the disassembly of the anode block. In addition, the decrease of the graphite portion to about 10 mm permits a reduction in the cost of the electrode. Moreover, the time required for replacing the electrodes is shortened, and the replacement operation needs no special skill. These effects and advantages make it possible to maintain a DC plasma jet generator in a hot cell by remote control, so that a DC plasma emission spectrochemical analysis system for a hot cell can be put into practical use, and thus the number of elements which can be analyzed in the cell is greatly increased. In addition, labor is reduced in the operation, and the efficiency is improved. Thus, it becomes possible to powerfully support the test and research on high-level radioactive materials.

It is, needless to say, obvious that the invention can be applied not only to a DC plasma jet generator installed in a hot cell, but also to a DC plasma jet generator installed in an ordinary laboratory or the like, so that the replacement of electrodes and the like can be effected easily.

It is to be understood that the foregoing description is a preferred embodiment of the invention and that various changes and modifications may be made in the invention without departing from the scope of the appended claims.

What is claimed is:

1. A DC plasma jet generator for emission spectrochemical analysis, comprising:
    a frame,
    first and second anode blocks pivotally mounted on said frame, respectively positioned along a first axial line and a second axial line, each terminating at one end thereof at a common central point;
    a cathode block pivotally mounted on said frame, positioned along a third axial line terminating at one end thereof at said common point, said first, second and third axial lines together defining a generally inverted Y shape having a base and two tips, said cathode block being positioned along said base, said cathode block including a cathode extending along said third axial line;
    said first and second anode blocks respectively including:
    first and second cylinders respectively extending along said first and second axial lines, each of said first and second cylinders having a first axial cylinder end and a second axial cylinder end between said first axial cylinder end and said common point,
    first and second cooling blocks respectively mounted on said second axial cylinder end of said first and second cylinders,
    first and second pistons, each having a first axial piston end and second axial piston end between said first axial piston end and said common point and having respective first and second recesses in said second axial piston end, respectively reciprocally movable axially in said first and second cylinders toward and away from said common point, said first and second recesses each having a first axial recess end and a second axial recess end between said first axial recess end and said common point,
    first and second rare earth metal magnets respectively mounted in said first and second recesses at said first axial recess end, and
    first and second anodes, each having a first axial anode end and a second axial anode end between said first axial anode end and said common point, respectively having said first axial anode end received in said first and second recesses, said first axial anode end being formed of a magnetically attractive metal so that the first axial anode ends of said first and second anodes are respectively attracted into said first and second recesses by said first and second magnets, said second axial anode end comprising a graphite rod, said first and second anodes and said cathode being simultaneously projectable toward said common point into contact thereat; and
    means for pivoting said first and second anode blocks and said cathode block into upright orientations so as to expose said first and second anodes and said cathode for upward removal and replacement.

2. A DC plasma jet generator for emission spectrochemical analysis according to claim 1, wherein said first and second recesses have respective configurations which respectively exactly fit said first axial anode end of said first anode and said first axial anode end of said second anode.

3. A DC plasma jet generator for emission spectrochemical analysis according to claim 1, wherein said pivoting means comprises respective rotary ratchet mechanisms for each of said anode and cathode blocks, so that each of said anode and cathode blocks can be positioned and fixed thereby at a predetermined pivotal position.

4. A DC plasma jet generator for emission spectrochemical analysis, comprising:
    a cathode and first and second anodes;
    first and second anode blocks respectively positioned along a first axial line and a second axial line, each terminating at one end thereof at a common central point;

a cathode block positioned along a third axial line terminating at one end thereof at said common point, said first, second and third axial lines together defining a generally inverted Y shape having a base and two tips, said cathode block being positioned along said base, said cathode being axially removably mounted on said cathode block, extending along said third axial line;

said first and second anode blocks respectively including:

first and second cylinders respectively extending along said first and second axial lines, each of said first and second cylinders having a first axial cylinder end and a second axial cylinder end between said first axial cylinder end and said common point, first and second cooling blocks respectively mounted on said second axial cylinder end of said first and second cylinders, first and second pistons, each having a first axial piston end and second axial piston end between said first axial piston end and said common point and having respective first and second recesses in said second axial piston end, respectively reciprocally movable axially in first and second cylinders toward and away from said common point, said first and second recesses each having a first axial recess end and a second axial recess end between said first axial recess end and said common point, and first and second rare earth magnets respectively mounted in said first and second recesses at said first axial recess end;

said first and second anodes each having a first axial anode end and a second axial anode end between said first axial anode end and said common point, and respectively having said first axial anode end received in said first and second recesses, said first axial anode end being formed of a magnetically attractive metal so that the first axial anode ends of said first and second anodes are respectively attracted into said first and second recesses by said first and second magnets, said second axial anode end comprising a graphite rod, said first and second anodes and said cathode being simultaneously projectable toward said common point into contact thereat; and a frame, said first and second anode blocks and said cathode block being pivotally mounted on said frame so that said first and second anode blocks and said cathode block are pivotable into upright orientations so as to expose said first and second anodes and said cathode for upward removal and replacement.

* * * * *